United States Patent
Huber et al.

(10) Patent No.: US 10,275,895 B2
(45) Date of Patent: Apr. 30, 2019

(54) MECHANISM FOR ADVANCED STRUCTURE GENERATION AND EDITING

(71) Applicant: Varian Medical Systems International AG, Cham (CH)

(72) Inventors: Michael Huber, Ag (CH); Michael Waschbuesch, Ag (CH); Lasse Toimela, Espoo (FI); Patrik Kunz, Ag (CH)

(73) Assignee: Varian Medical Systems International AG, Cham (CH)

( * ) Notice: Subject to any disclaimer, the term of this patent is extended or adjusted under 35 U.S.C. 154(b) by 650 days.

(21) Appl. No.: 14/473,756

(22) Filed: Aug. 29, 2014

(65) Prior Publication Data
US 2015/0055848 A1    Feb. 26, 2015

Related U.S. Application Data

(63) Continuation of application No. 12/821,985, filed on Jun. 23, 2010.

(51) Int. Cl.
*G06T 7/33* (2017.01)
*A61N 5/10* (2006.01)

(52) U.S. Cl.
CPC .............. *G06T 7/33* (2017.01); *A61N 5/103* (2013.01); *G06T 7/337* (2017.01); *G06T 2207/10081* (2013.01); *G06T 2207/10088* (2013.01); *G06T 2207/10116* (2013.01); *G06T 2207/20096* (2013.01); *G06T 2207/30096* (2013.01)

(58) Field of Classification Search
CPC .. G06T 7/38; G06T 7/70; G06T 7/149; G06T 2207/30004; G06T 7/0012; G06T 2200/04; G06T 2207/30096; G06T 2219/2021; G06K 9/6206; A61B 34/10
See application file for complete search history.

(56) References Cited

U.S. PATENT DOCUMENTS 7,231,076 B2  6/2007 Fu et al.
7,792,348 B2  9/2010 Russakoff
(Continued)

OTHER PUBLICATIONS

Jie Shao et al., "Shape-Regulated Particle Filtering for Tracking Non-Rigid Objects" .Image Processing, 2006 IEEE International Conference on, IEEE, PI., Oct. 1, 2006, pp. 2813-2816.
(Continued)

*Primary Examiner* — Joseph D Burgess

(57) ABSTRACT

Embodiments of the present invention are directed to methods and a mechanism for manipulating images generated by radiotherapy machines used in radiation diagnostic and treatment applications. In one embodiment, a method is provided for intelligent automatic propagation of manual or automatic contouring across linked (e.g., registered) images and image data sets by acquiring one or more images of one or more image data sets; determining the correlation between the images with respect to identified structures; and generating a deformation map that establishes a correspondence for each point in the source image with a point in the target image. Subsequently, the intelligent propagation mechanism applies this deformation map individually to each structure of the source image and propagates the deformed structure to the target image.

22 Claims, 7 Drawing Sheets

(56) References Cited

U.S. PATENT DOCUMENTS

| | | | |
|---|---|---|---|
| 2003/0007601 A1* | 1/2003 | Jaffray | A61B 6/032 |
| | | | 378/65 |
| 2003/0095721 A1* | 5/2003 | Clune | A61B 1/00009 |
| | | | 382/294 |
| 2005/0196027 A1 | 9/2005 | O'Donnell et al. | |
| 2005/0251029 A1* | 11/2005 | Khamene | A61B 8/4245 |
| | | | 600/427 |
| 2006/0274061 A1 | 12/2006 | Wang et al. | |
| 2006/0291696 A1 | 12/2006 | Shao et al. | |
| 2007/0189591 A1* | 8/2007 | Lu | A61N 5/103 |
| | | | 382/128 |
| 2008/0043017 A1* | 2/2008 | Xue | G06T 19/20 |
| | | | 345/424 |
| 2008/0144939 A1 | 6/2008 | Russakoff | |
| 2008/0159612 A1 | 7/2008 | Fu et al. | |
| 2008/0219406 A1 | 9/2008 | Kaus et al. | |
| 2009/0067692 A1* | 3/2009 | Breeuwer | G06T 7/33 |
| | | | 382/128 |
| 2011/0268330 A1* | 11/2011 | Piper | G06K 9/6207 |
| | | | 382/131 |

OTHER PUBLICATIONS

Peroni et al.,"Validation of an Automatic Contour Propagation Method for Lung Cancer 4D Adaptive Radiation Therapy", Biomedical Imaging: From Nano to Macro, 2009. ISBI'09 IEEE Piscataway, NJ, USA, Jun. 28, 2009, pp. 1071-1074.

* cited by examiner

Exemplary Computer System 700

MECHANISM FOR ADVANCED STRUCTURE GENERATION AND EDITING

RELATED APPLICATIONS

This application is a continuation of, and claims the benefit of U.S. patent application Ser. No. 12/821,985 filed Jun. 23, 2010, which is incorporated herein by reference and for all purposes.

TECHNICAL FIELD

The present invention pertains generally to radiation therapy and, in particular, involves a mechanism for manipulating images generated by radiotherapy machines used in radiation diagnostic and treatment applications.

BACKGROUND

The usage of medical imaging devices to diagnose and plan treatment for various internal ailments is well known. Often, an imaging device such as an X-ray device, Computer Tomography (CT), or Magnetic Resonance Imaging (MR) device is used to generate one or more initial scans or images of the area of interest. These initial scans may be acquired by focusing a beam of radiation into a target volume and collecting the traversing beams in an imager. The beams collected by the imagers are used to generate a display (i.e., one or more images) of the targeted volume that may be used to diagnose or monitor an afflicted area (e.g., a tumor or lesion or a surrounding area).

Typically, once an image has been acquired, critical structures (e.g., regions or organs) disposed in the target area must be specifically identified so that treatment may be optimally directed. Conventional medical imaging techniques include techniques for automatically identifying ("segmenting") organs and large structures. These techniques often include delineating adjacent structures by derived radiodensities and classifying the structures according to their relative positions and derived densities with known values. However, even with automatic segmentation of anatomical structures, identification of these regions often also includes tracing the outline ("contouring") of these or other structures. For example, radiation targeting a specific organ or a portion of an organ may require specific identification and/or demarcation of the portion(s) of the organ to receive treatment. Likewise, tumors can also be specifically contoured and identified for treatment. For certain treatment plans, it may be preferred to designate these identified portions by specifically contouring the circumference of the area.

Traditionally, this contouring has been performed manually and this process is performed at least once on a diagnostic planning CT, with the generated structures subsequently being used for calculation of the treatment plan. Newer technology and advanced techniques allow for improved image collection through the use of a cone-beam computerized tomography system (CBCT). In conventional computerized tomography systems, one or more 2D slices are reconstructed from one dimensional projections of the patient, and these slices may be combined to form a three dimensional (3D) image of the patient. A cone beam computerized tomography system is similar to that of a conventional computerized tomography system, with the exception that an entire volumetric image is acquired through rotation of the source and imager, and a fully 3D image is reconstructed from a plurality of 2D projections. Unfortunately, manually drawing the individual contours on a contiguous set of 2D slices then combining them for each image of an entire data set can be extremely time consuming and labor intensive. The time and labor increases even more with the number of image slices and the number and respective sizes of the anatomical structures (e.g., organs, tumors, etc.) in the particular area of interest.

Moreover, specific anatomies may change (sometimes drastically) over time and/or as a result of receiving radiation treatment over the course of a treatment plan. Specifically, the target volumes may expand or reduce in size, depending on the ailment and the efficacy of the treatment plan. As such, treatment plans designed around diagnostic images generated during an initial CT scan may be ineffective, inefficient, or even dangerous to treat patients. In order to ensure optimal targeting and positioning, updated images of the treated area are sometimes acquired periodically by generating additional images during the treatment process to ensure an appropriate positioning of the therapeutic radiation beam and to determine the effectiveness of the treatment regimen. Recently developed treatment machines allow for the detection of anatomical changes by employing advanced imaging acquisition techniques such as cone-beam computer tomography (CBCT) at the site of the treatment machine, often either immediately before or after treatment is administered to the patient.

While the timing of the updated image generation and treatment may differ according to the particular patient and/or treatment plan, some treatment plans include monitoring by acquiring monitoring images on a daily basis. Unfortunately, reliance on updated images also increases the contouring workload, particularly if the data is used for plan adaptation since any additional contouring that was manually performed is typically not preserved over additional image generation and through the application of conventional automatic segmentation techniques. Due to its sensitive nature, manual contouring of and within anatomical structures for treatment purposes can be very time consuming. As such, manually replicating contouring for a multitude of images can be an extremely intensive and inefficient process.

SUMMARY

This Summary is provided to introduce a selection of concepts in a simplified form that is further described below in the Detailed Description. This Summary is not intended to identify key features or essential features of the claimed subject matter, nor is it intended to be used to limit the scope of the claimed subject matter.

Manual contouring is still a time consuming process in radio therapy planning. Typically, this process is done once on a diagnostic planning CT and the generated structures are subsequently used for calculation of the treatment plan. However with increased availability of imaging modalities during the treatment process (e.g., daily cone beam CT at the treatment machine), the request for efficient contouring tools or sophisticated concept to adapt the original contours/structures to the new anatomical situation has increased. Embodiments of the present invention are directed to methods and a mechanism for automatically propagating contoured features across multiple image data sets generated by radiotherapy machines used in radiation diagnostic and treatment applications.

According to embodiments of the present invention, anatomical structures which have been defined on one image (e.g., the 3D CT used at the planning stage) can be automatically propagated to another 3D image data set (e.g., CBCT acquired on the treatment machine), given the condition that the two data sets have been pre-registered to each other. In one embodiment, a method is provided for intelligent automatic propagation of manual or automatic contouring across linked (e.g., registered) images and image data sets. As provided, the method includes acquiring one or more images of one or more image data sets, determining the correlation between the images with respect to identified structures, generating a deformation map that establishes a correspondence for each point in the source image with a point in the target image. Subsequently, the intelligent propagation mechanism applies this deformation map individually to each structure of the source image and propagates the deformed structure to the target image. This allows automatic propagation of generated contouring and local structural changes to structures in a given data set or between disparate data sets while accounting for content deviation as a result of time and/or treatment that may exist between the images.

The advantages provided by performing this method include enabling structure copy functionality that incorporates the knowledge from the deformation map to provide a more accurate match to the actual anatomy in the target image. The same tools designed for correction of the deformation field from image registration can also be used to correct features simultaneously on the two or more registered images to enable simultaneous contouring on multiple registered data sets. In addition, the efficiency of editing of multiple structures simultaneously may be realized.

BRIEF DESCRIPTION OF DRAWINGS

The accompanying drawings, which are incorporated in and form a part of this specification, illustrate embodiments of the invention and, together with the description, serve to explain the principles of the invention.

DETAILED DESCRIPTION

Figure 1:
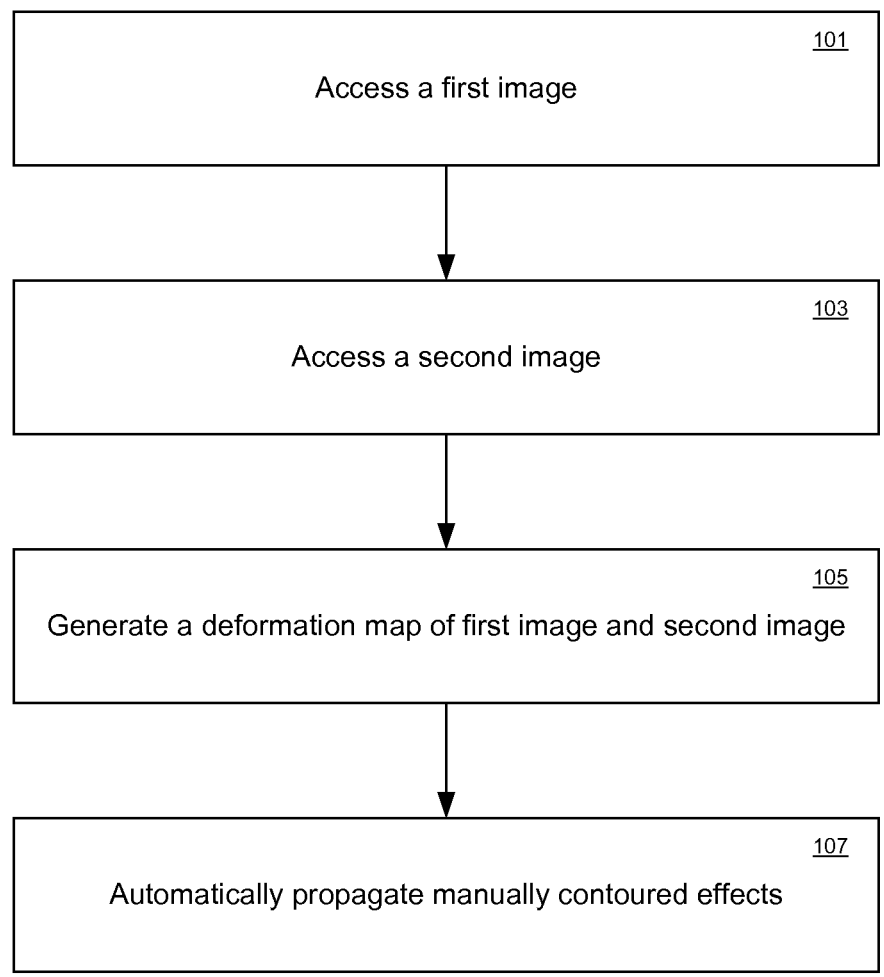
FIG. 1 depicts a flowchart of a method for automatically propagating defined structures across a plurality of associated data sets, in accordance with embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, and components, have not been described in detail as not to unnecessarily obscure aspects and features of the subject matter.

Portions of the detailed description that follows are presented and discussed in terms of a method. Although steps and sequencing thereof are disclosed in figures herein (e.g., FIGS. 1, 2) describing the operations of this method, such steps and sequencing are exemplary. Embodiments are well suited to performing various other steps or variations of the steps recited in the flowchart of the figure herein, and in a sequence other than that depicted and described herein.

Embodiments described herein may be discussed in the general context of computer-executable instructions residing on some form of computer-usable medium, such as program modules, executed by one or more computers or other computing devices. Generally, program modules include routines, programs, objects, components, data structures, etc., that perform particular tasks or implement particular abstract data types. The functionality of the program modules may be combined or distributed as desired in various embodiments.

By way of example, and not limitation, computer-usable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, random access memory (RAM), read only memory (ROM), electrically erasable programmable ROM (EEPROM), flash memory or other memory technology, compact disk ROM (CD-ROM), digital versatile disks (DVDs) or other optical storage, magnetic cassettes, magnetic tape, magnetic disk storage or other magnetic storage devices, or any other medium that can be used to store the desired information.

Communication media can embody computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

In the following embodiments, a technique to automatically propagate manually contoured effects among a plurality of data sets in an imaging system is described. Embodiments include a method for automatically propagating manually contoured effects from a source image to associated target images while adjusting for differences between the referenced images.

Automatic Propagation of Contoured Structures to Associated Data Sets

FIG. 1 is a flowchart 100 of a method for automatically propagating manually or automatically contoured structures across a plurality of images in accordance with one embodiment. Steps 101-107 describe exemplary steps comprising the process depicted in flowchart 100 in accordance with the various embodiments herein described. In one embodiment, the flowchart 100 is implemented as computer-executable instructions stored in a computer-readable medium and performed by a computing device executing a process for automatically propagating manually contoured effects among data sets.

At step 101, a first image comprising a first plurality of structures and one or more manually or automatically contoured effects is accessed. The first image may comprise, for example, a first data scan of a CT data set generated by a medical imaging device. The first image may also consist of the display of data acquired during an initial diagnostic CT scan. According to some embodiments, data for the entire data set may be pre-imaged and stored in a data storage repository (such as a memory), which is accessed at step 101. In some instances, the first image may itself comprise a plurality of anatomical features or structures. These features may include, but are not limited to, organs, tumors, lesions and the like. Some or all of these features may be automatically segmented according to various identification and segmentation techniques implemented as software programs. In further embodiments, an image may display features which may comprise a plurality of contoured effects, such as outlined regions or portions of structures.

At step 103, a second image comprising a second plurality of structures is accessed. For example, the second image may comprise a display of the same anatomical region(s) and for the same (or even different) patient. The second image may comprise, for example, a second data scan of a data set generated by a medical imaging device. The medical imaging device may comprise the same imaging device as the imaging device which generated the data for the first data set. In some embodiments, the second image may be of the same data set as the first image. Alternatively, other imaging devices may also be used to generate the second data set. For example, in some instances, a radiation therapy machine may be equipped with CBCT or other imaging equipment. A patient receiving treatment from a radiation therapy machine may also be imaged by the imaging equipment. Other devices, such as magnetic resonance imaging devices or other similar medical imaging devices may also be used to acquire image data.

In one embodiment, a computing device performing step 103 may be communicatively coupled to the treatment and/or imaging equipment, thereby allowing the data comprising the second image, once acquired, to be accessed immediately by the executing computing device. Alternatively, data for one image or the entire data set may be likewise pre-imaged and stored in the data storage repository that was accessed at step 101.

The second image may, as with the first image, comprise a plurality of anatomical features. These features may include, but are not limited to all or a portion of the structures displayed in the first image. In some embodiments, the second image may consist of a display of an equivalent or substantially equivalent general anatomical region displayed in the first image, with an equivalent or substantially similar orientation, axes, dimensions, scope. Alternatively, the second image may comprise a display of a different plurality of anatomical features, wherein only portions of the anatomy displayed in the first image are visible, and which may differ in orientation, or other visual configurations and conditions with the display of the features in the first image. According to some embodiments, the second image may be pre-associated with the first image. Pre-association may include registration within a system.

At step 105, any disparities of specifically identified content common to both the first image accessed at step 101 and the second image accessed at step 103 are identified and the relationships between points of disparities are mapped. Mapping the dissimilarities of the common features may be performed by generating a "deformation map" of the two images. In one embodiment, the deformation map may be generated by establishing a correspondence for each pixel of a common structure or anatomical region in the first or "source" image with an equivalent pixel in the second or "target" image. The positions of the pixels are compared and the relative displacement between a pair of corresponding pixels is then determined to derive a relativity between the pixels. In one embodiment, corresponding pixels are identified by comparing the respective pixel intensities relative to the rest of the image. This correspondence may be implemented as a three dimensional vector field, for example. Alternatively, the correspondence may also be implemented by a plurality of mathematical functions which express the relativity between two corresponding points.

At step 107, manually or automatically contoured effects identified in the first image accessed at step 101 are automatically propagated to the second image accessed at step 103 according to the deformation map generated at step 105. In some embodiments, the contoured effects may be propagated automatically to every image registered to the first image (or every data set registered to the data set of the first image).

Propagating the contoured effects may be performed, for example, by applying the deformation map to the contoured effects and copying the resulting output on to the second image. That is, rather than an explicit 1:1 propagation of identically contoured effects, any manually or automatically contoured effects from the first image will be propagated to the second image while being adjusted to the mapped disparities between the two images. For example, if, after treatment, the size, position, and/or shape of a tumor have been modified, an area surrounding the tumor which has been contoured for specific targeting would, ideally, be also modified correspondingly for optimal targeting of treatment. Where a one to one propagation has been effected, any contouring of a target may be inappropriately sized (e.g., either of insufficient size or specificity), in a non-corresponding position, or a non-conforming and non-ideal shape. By applying a deformation map to the propagation of contoured effects, a more specific and accurate propagation can be performed.

Propagation of Contoured Structures to Updated Images of a Data Set

Figure 2:
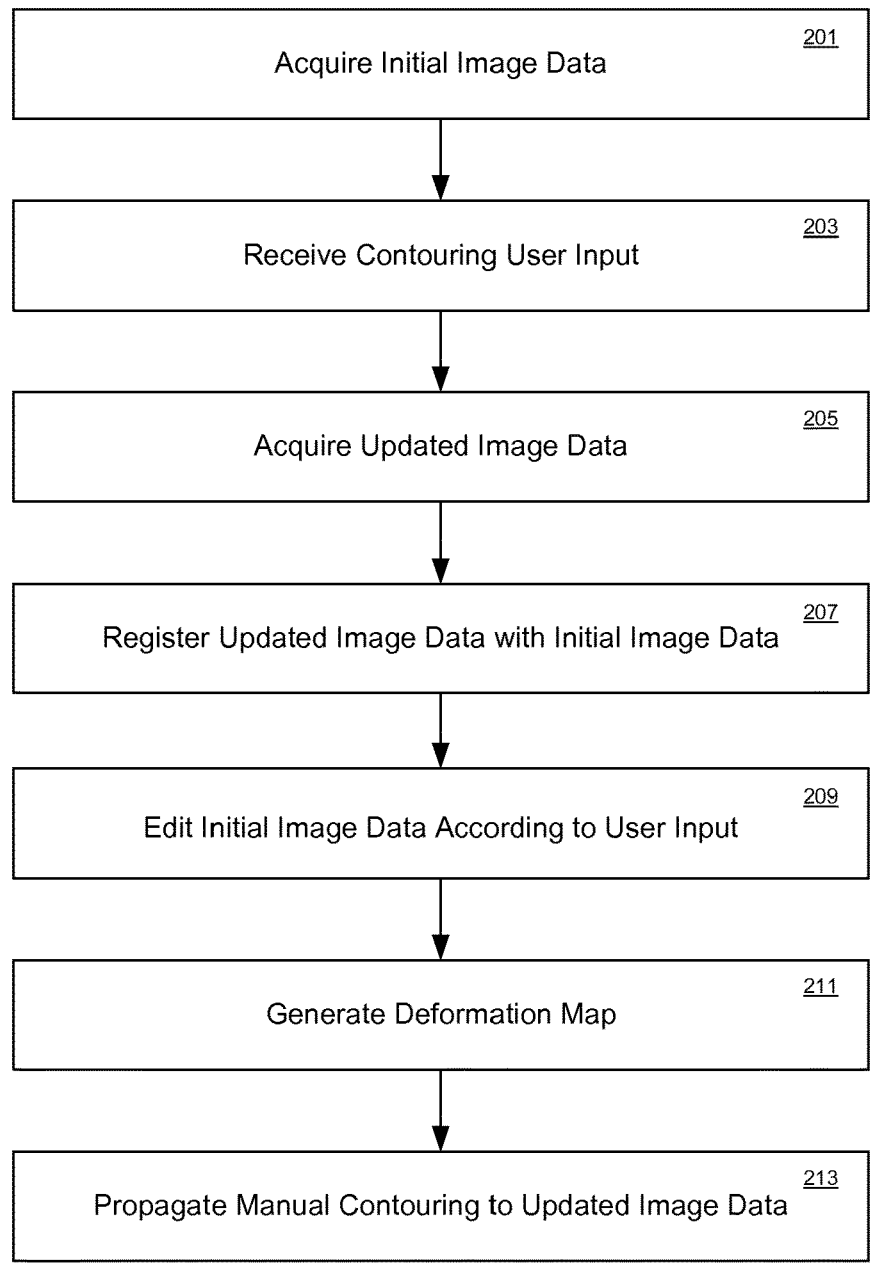
FIG. 2 depicts a flowchart of a method for propagating updated contouring data between updated images in a single data set, in accordance with embodiments of the present invention.

FIG. 2 depicts a flowchart of a method for propagating updated structural contouring data among a plurality of data sets, in accordance with embodiments of the present invention. Steps 201-213 describe exemplary steps comprising the process depicted in flowchart 200 in accordance with the various embodiments herein described. In one embodiment, the flowchart 200 is implemented as computer-executable instructions stored in a computer-readable medium and performed by a computing device executing a process for automatically updating structural contouring data among a plurality of data sets.

At step 201, initial image data of a target subject is acquired by an imaging device. In one embodiment, the image data comprises a display of a portion of the target subject's anatomy. Acquisition of the initial image data may be performed by generating image data of a plurality of images in a data set in an imaging device such as an X-ray, MRI, or other medical imaging device. According to various embodiments, the initial image data may be acquired during, or in furtherance of, a diagnostic procedure. Once acquired, the initial image data may be stored for future reference. In one embodiment, initial image data may be stored by, accessed from, and manipulated in a dedicated software application. User input received through a graphical user interface of the software application may direct the storage, access, and manipulation of the file(s) comprising the image data.

The initial image data acquired by the imaging device in step 201 may comprise a plurality of anatomical structures (e.g., organs, tumors, lesions, etc.). Some or all of these structures may be automatically segmented according to various identification and segmentation techniques implemented as software programs. In some embodiments, additional contouring corresponding to user input may be received at step 203, for the purposes of treatment planning, for example.

The contouring may be manually added, through user input received in a graphical user interface executing on a computer system, for example. Alternatively, the contouring may be automatically derived from contouring algorithms. Examples of contouring may include effects such as explicit outlining of regions of all or a portion of one or more structures. In one embodiment, user input may be acquired by displaying an image corresponding to the image data, and receiving user input via cursors and other user input devices, the input indicating the desired manual contouring on the display.

At step 205, updated (e.g., chronologically subsequent) image data of the target subject is acquired. Updated image data may consist of a display of the target area of the same subject acquired the initial image data at a subsequent point in time. Updated image data may be acquired, for example, after a diagnostic process and during the course of treatment. For example, the image data may be acquired by a treatment device equipped with CT or CBCT imaging device. Updated image data may also be acquired in subsequent sessions of the same diagnostic process in which the initial image data was acquired, and generated by the same imaging device as the imaging device which generated the initial image data.

In one embodiment, the same or a substantial majority of structures depicted in the image according to the initial image data may also be depicted in the updated image data. For example, the updated image data may represent a display of the same or substantially equivalent anatomical region(s) for a target subject (e.g., a patient or a portion of a patient's anatomy). Alternate embodiments may include less or greater amounts of structures, or a like number of structures, with varying degrees of orientation, position, and axial disposition, such that at least one structure is in common between the updated image data and the initial image data.

At step 207, a relationship between the updated image data and the initial image data is established. In one embodiment, establishing a relationship between the updated image data and the initial image data may be performed by registering the respective data in an image software application. Registration may be performed by receiving manual input from a user (through a user interface, for example) which associates a file comprising the updated image data with a file comprising the initial image data within an image editing or viewing application. In alternative embodiments, the relationship may be pre-defined prior to the acquisition of the updated image data. For example, images identified for a particular subject or patient may be automatically related (e.g. registered) within the application once the image data is acquired. According to some embodiments, multiple images may be registered together simultaneously. For example, a data set comprising multiple images may be registered automatically. Alternatively, entire data sets may be related to each other, such that each image of each data set is mutually associated with every other image of every data set within the application.

The initial image data may be edited at step 209 to include the contouring received at step 203. Editing the initial image data may be performed by, for example, adding the data corresponding to the contouring to the initial image data. In further embodiments, the edited initial image data may be stored for future reference. At step 211, a mapping mechanism is generated for cataloguing any content deviation determined between the initial and updated image data. In one embodiment, the mapping mechanism may be implemented as a deformation map derived by comparing the updated image data with the initial image data and determining the presence of deviations of common image features between targeted and identified features common to both images. In some embodiments, a deformation map may be generated for each image in a pairing, wherein the deviation of common features may be mapped while non common features may be disregarded during the mapping procedure. Alternatively, a distinct deformation map for each common feature within an image data pairing may be generated.

According to some aspects, content deviation may be detected by comparing pixel data of the pixels comprising one or more common features in the initial image data to pixel data of the common features in the updated image data. For example, relative pixel intensities of the pixels comprising a common feature of the initial image data may be compared to pixel intensities of the pixels comprising the same feature on the updated image data. In such fashion, a correspondence between pixels for the same features on different images may be derived, and a deformation map (or other such mechanism) may be generated. This correspondence may be represented as a three dimensional vector field and/or expressed by a plurality of mathematical functions which define the relativity between two corresponding points.

At step 213, the manually (or automatically) contoured effects identified in the initial image data received at step 203 are automatically propagated to the updated image data acquired at step 205 according to the mapping mechanism (e.g., deformation map) generated at step 211. In some embodiments, the contoured effects may be propagated automatically to every image registered to the initial image (or every data set registered to the data set of the initial image). According to certain embodiments, a generated deformation map is invertible, and, accordingly, once a deformation map has been generated, contoured effects received for updated image data may be propagated to the initial image data according to the same process.

Propagating the contoured effects may be performed according to step 107 described above with respect to FIG. 1. Thus, for example, any contoured effects may be propagated by applying the deformation map (or other mapping mechanism acquired at step 211) to the contoured effects in the initial image and adding the resulting output to the data of the updated image (or vice versa). Accordingly, rather than an explicit 1:1 propagation of identically contoured effects, any contoured effects from the initial image will be propagated to the updated image while automatically being adjusted to the mapped disparities between the two images, therefore resulting in a propagation of the contoured effects that is specific and customized to the more recent image data. Likewise, a propagation of contoured effects from an updated image to the initial image will create corresponding contoured effects on the initial image that are customized for the initial image.

Exemplary Automatic Propagation of Contoured Structures

Figure 3:
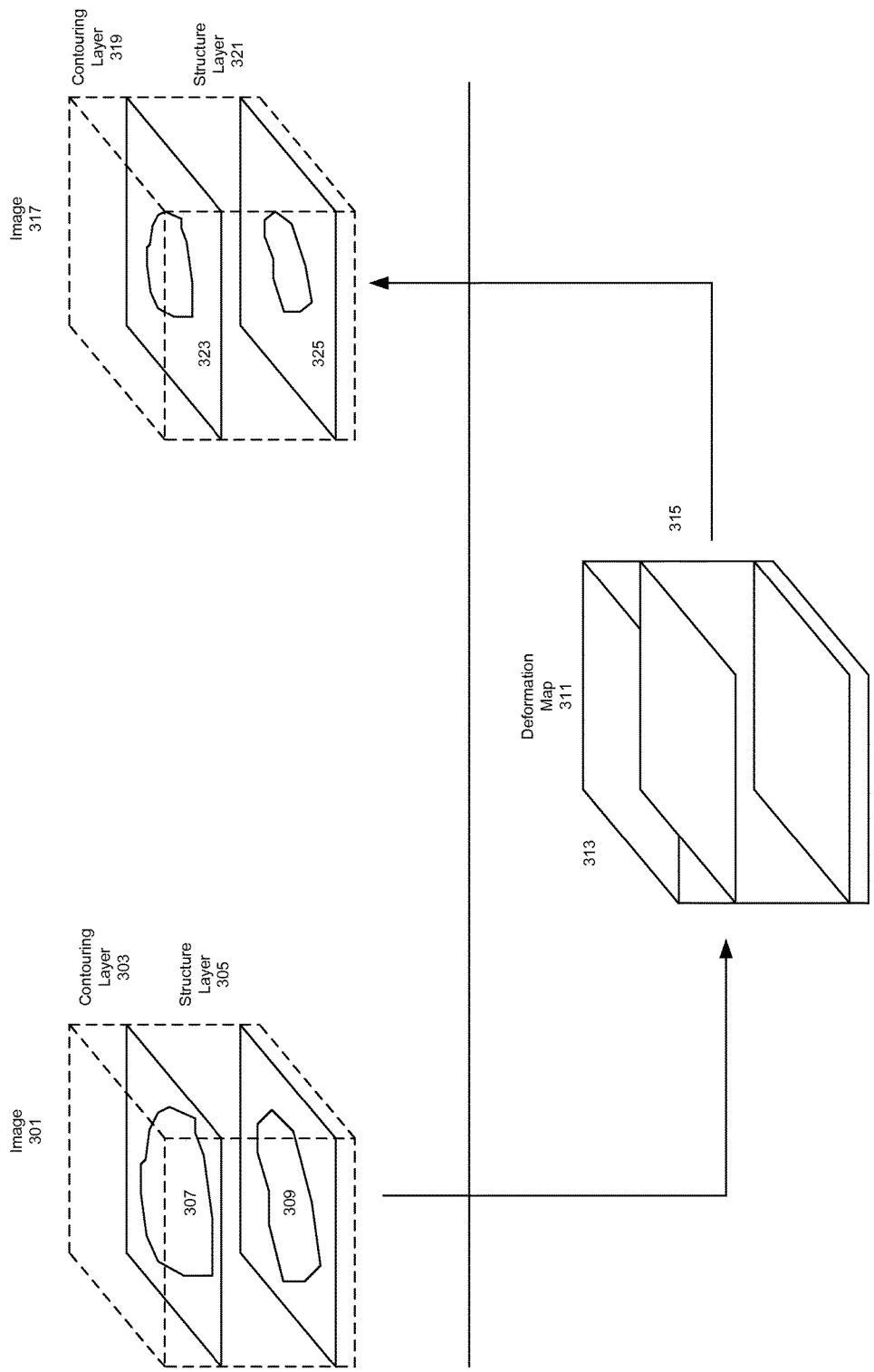
FIG. 3 is an illustration of an exemplary propagation between related images in a data set, in accordance with embodiments of the present invention.

FIG. 3 is an illustration of an exemplary propagation between related images in a data set. According to some embodiments, a first image 301 and an associated second image 317 may represent images of a portion of a subject anatomy generated from a medical imaging system, for example, such as CT images or CBCT images. These images may include structures such as organs, or vessels or other anatomical units. In some embodiments, these structures may be manually (e.g., through a user interface) or automatically (e.g., through a software procedure) delineated and identified.

According to one aspect, the first image may comprise an earlier "source" image generated from (and graphically representing) a portion of a subject anatomy and the second image may comprise a chronologically later "target" image of the same or similar portion of the subject anatomy. For example, the source image may be generated from a subject during an earlier diagnostic period, whereas the target image may be generated from the same subject at a later date, after a treatment or routine has been applied. Alternatively, the target image may also be generated from a different subject (e.g., patient) but comprise a display of the same or substantially similar portion of an anatomy.

During typical diagnostic and treatment processes, the image data generated by medical imaging devices may be enhanced by manual or automatic contouring. The contouring may be used, for example, to delineate, emphasize or target specific portions of the image. As presented in FIG. 3, manually or automatically contoured effects in the first or "source" image 301 may be automatically propagated to a second, associated "target" image 317 through the execution of the methods described above with respect to FIGS. 1 and 2.

Under certain conditions, the association between the first and second image (image 301, and image 317, respectively) may be pre-defined within an application, such as an image manipulation and/or image display application. According to other configurations, the association may be definitively and explicitly established through received manual input (e.g., from a user through an on-screen user interface). In further configurations the associations may be automatically established once certain pre-conditions are met (e.g., same identified subject, same identified storage location, etc.)

As depicted in FIG. 3, images within a data set may further comprise one or more layers. For example, the first image 301 is presented with a plurality of layers (e.g., layers 303, 305). According to some embodiments, the identified features may be grouped and/or arranged among the one or more layers. For example, for embodiments wherein the image represents a subject's anatomy, organs may be presented on one layer, the cardiovascular system may be presented on a second layer, and the skeletal system may be presented on a third, etc. In still further embodiments, contoured effects may be separated from other features and arranged within an exclusive layer.

The layers comprising the first image 301 may correspond to layers of the second image 317. Thus, for example, contour layer 319 of the second image 317 corresponds to contour layer 303 of the first image 301, and feature layer 321 of the second image 317 corresponds to feature layer 305 of the first image 301. According to these embodiments, like-identified layers among associated images may be automatically associated within an application or platform. Alternatively, user-defined associations may also be created.

As presented in FIG. 3, image 301 includes a feature layer 305 that includes a feature (e.g., feature 309). The feature may, for example, represent an anatomical organ or other region in a target anatomy. Likewise, the same anatomical organ or region may also be represented in the feature layer 321 of the second image 317 as feature 325. As shown in FIG. 3, feature 325 appears smaller than feature 309. According to some embodiments, the specific pixel disparities between two features or units within a pair (or more) of images may be mapped by a deformation mechanism (e.g., deformation map 311). As presented in FIG. 3, mapping may be performed by determining correspondences in the pixels comprising one or more features (e.g., feature 309 and feature 325).

As depicted in FIG. 3, the correspondences may be mapped by generating a map of pixels for each image. Each pixel map (e.g., deformation map) may be generated specifically for each image, and plots the spatial relativity between the features (via pixels) comprising the image in the deformation map. A correspondence between the deformation map of the first image 301 and the deformation map of the second image 317 may be mapped by, for example, determining relative pixel intensities of the pixels comprising the feature on each image, determining a correspondence (e.g., an equivalence) between a pixel in the first image 301 and a pixel in the second image 317 based on the pixel intensities, and determining the relative displacement between related pixels in the respective deformation maps of the images.

Thus, for example, the pixel intensity for any pixel in structure 309 relative to adjacent pixels may be determined and associated with a pixel in structure 325 with the same or substantially equivalent relative pixel intensity. A one to one mapping may be generated for each pixel of the structure(s) comprising the images 301, 317. Once the pixels comprising each feature are associated with an equivalent pixel in a related image, the relative displacement between each pixel of the source image 301 and its equivalent pixel in the target image 317 may be determined and mapped.

This relative displacement may be implemented as a registration map (e.g., 311) mapping the relativities between a plurality of deformation maps representing each respective image (301, 317). Thus, for example, the specific deformation between each pixel in deformation map 313 (corresponding to image 301) and deformation map 315 (corresponding to image 317) may be determined as a vector, with the aggregated relativities comprising a vector field. Other points of data (e.g., pixel) within image 301 may be thus similarly modified for image 317 by applying an equivalent or substantially equivalent vector. In alternate embodiments, in lieu of generating a vector field, the underlying algebraic equations that express the vectors comprising the vector field may be used to determine deformation (displacement).

Once the deformation mechanism 311 has been generated, contoured effects in one image may be propagated to another associated image. As depicted, the contoured structure 307 in the contour layer 303 may be propagated in the contour layer 319 of image 317. However, unlike conventional methods that are capable of only explicit duplication, the replicated effects may be modified according to the deformation mechanism 311 to more accurately reflect the subject anatomies. Thus, for example, if the relativity between feature 309 and feature 325 includes a change (e.g., a change in dimension, shape, axis, orientation, etc.), an equivalent change may be experienced by the contoured effect, once propagated. As depicted in FIG. 3, exemplary feature 325 comprises a smaller total area than feature 309. Likewise, the contoured effect 307, once adapted by the deformation mechanism 311, may also be reflected as a smaller total area in the second image as contoured effect 323, thereby providing automatic propagation that provides an adaptive output responsive to any changes over time.

Exemplary Local Structure Editing

Figure 4:
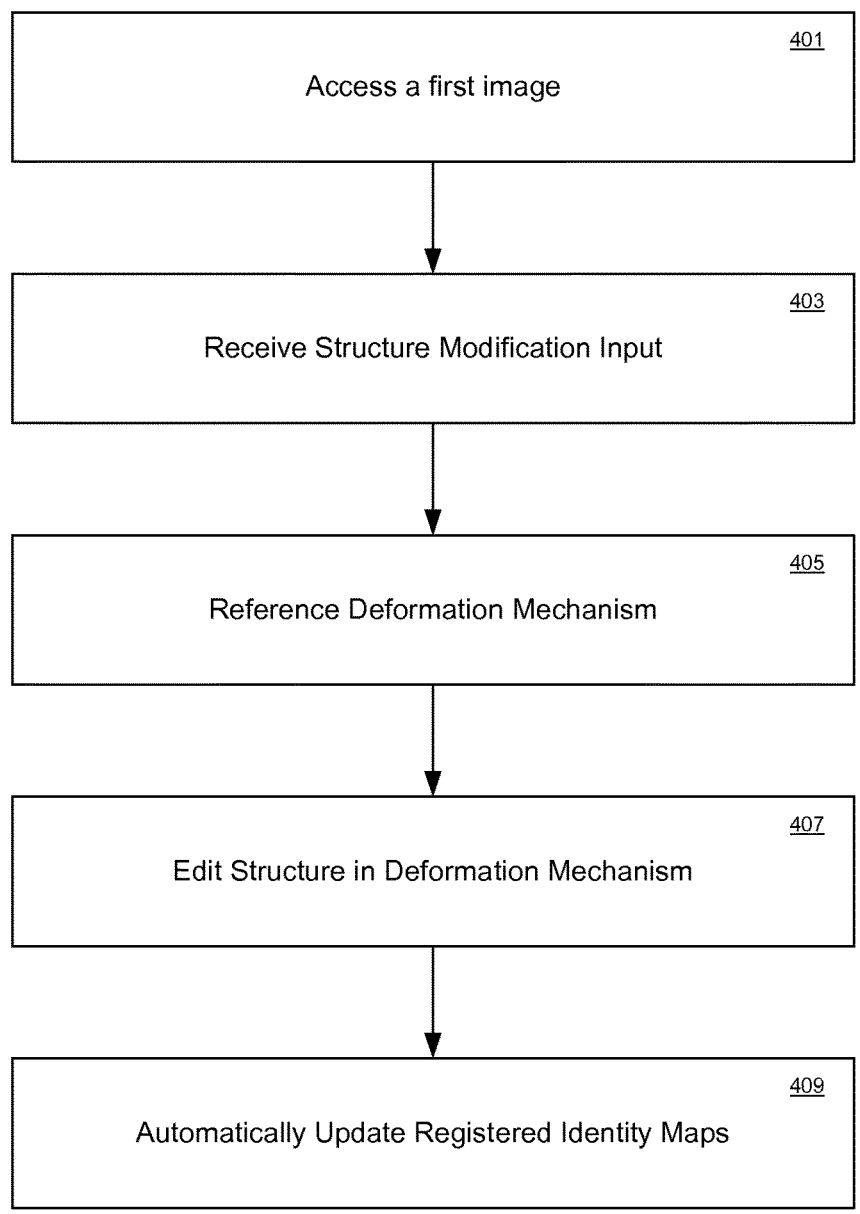
FIG. 4 depicts a flowchart of a method for automatically editing structures a plurality of related images, in accordance with embodiments of the present invention.

FIG. 4 depicts a flowchart of a method for editing local structures in one or more data sets, in accordance with embodiments of the present invention. Steps 401-409 describe exemplary steps comprising the process depicted in flowchart 400 in accordance with the various embodiments herein described. In one embodiment, the flowchart 400 is implemented as computer-executable instructions stored in a computer-readable medium and performed by a computing device executing a process for automatically editing structural data among one or more data sets.

At step 401, a first image is accessed by, for example, a computing device executing an image manipulation software application. In one embodiment, the image data represents a graphical display of a portion of the target subject's anatomy, such as data acquired according to a diagnostic procedure (e.g., X-ray, MRI, etc.) In particular, anatomical structures (e.g., organs, vessels, system units) may be depicted within the graphical display. In still further embodiments, the image may have a corresponding deformation mechanism that maintains the relativity between the image and other registered images. In one embodiment, the deformation mechanism may be implemented to include an identity map and a registration map. According to such embodiments, the identity map may be used to map the relative positions of the anatomical structures within the same image.

The identity map may be implemented as, for example, a coordinate grid representing a two or three dimensional space, wherein a plurality of structures occupies space within the grid. A specific position of any point within such a space may be expressed as a set of values or coordinates, with each structure being the aggregate of a plurality of points. Thus, the identity map may be implemented by mapping the relative position of specific points comprising each structure to the points of adjacent structures. In one embodiment, the image data may be stored by and accessed from the same image manipulation software application. User input received through a graphical user interface of the software application may direct the storage, access, and manipulation of the file(s) comprising the image data within the computing device executing the application, or other communicatively coupled computing devices.

The registration map may be implemented as a linked series of identity maps corresponding to pre-associated images. Common structures shared between an identity map of an image and an identity map corresponding to another associated image may be mapped together within the registration map.

According to some embodiments, an input corresponding to a manual adjustment or editing of one or more structures of the first image (local structures) may be received at step 403. The structures, which are "local" to (e.g., disposed on) the image being viewed or edited, may be adjusted for accuracy, by correcting an artifact or to clarify one or more generated structures, for example. In further embodiments, previous manual contouring performed according to user input may be corrected or adjusted. The structural editing may be received through a graphical user interface generated by a software application. In one embodiment, user input may be acquired by displaying an image corresponding to the image data, and receiving user input via one or more cursors and other user input devices, the input indicating the desired structural on the display. For example, an outline or shape of a structure may be thus edited.

At step 405, the deformation mechanism corresponding to the first image is referenced. Referencing the deformation mechanism may be achieved by the executing software application on data stored in memory of a computing system, for example. At step 407, the structure corresponding to the user input received at step 403 is edited by editing the identity map of the first image in the deformation mechanism according to the user input. Thus, for example, the plurality of pixels that comprise the structure to be edited may be adjusted in the identity map to conform to, and represent, the structure as edited to take into account the user input received at step 403. In certain embodiments, an additional identity map may be created for the edited structure, and mapped to the original identity map corresponding to the first image. The unedited structures may be duplicated in the new identity map and modified to conform to the same relativity mapped between the structure prior to editing in the original identity map and the edited structure in the newly created identity map. Modifying the structures may be performed by, for example, modifying the values corresponding to one or more points comprised in the modified structure in the identity map.

At step 407, the manual structural edits to the first image received as user input at step 403 are automatically propagated to the other structures of the first image according to the identity map corresponding to the first image. In further embodiments, the effects of the structural edit may be propagated automatically to every other image registered to the first image (or every data set registered to the data set of the first image), as described below with respect to FIG. 6.

Propagating the structural edits may be performed by applying the deformation mechanism (e.g., the identity map and/or the registration map) to the first image and adjusting the remaining structures to account for the effect of the edited structure according to the identity map. Accordingly, rather than an explicit 1:1 propagation of identically edited effects, the structures in the first image will retain their relative sizes and positions (e.g., orientation, proportionality). Therefore resulting in a propagation of the effect of the initial structural edits to the other local structures that is specific and customized to the original image data.

Figure 5:
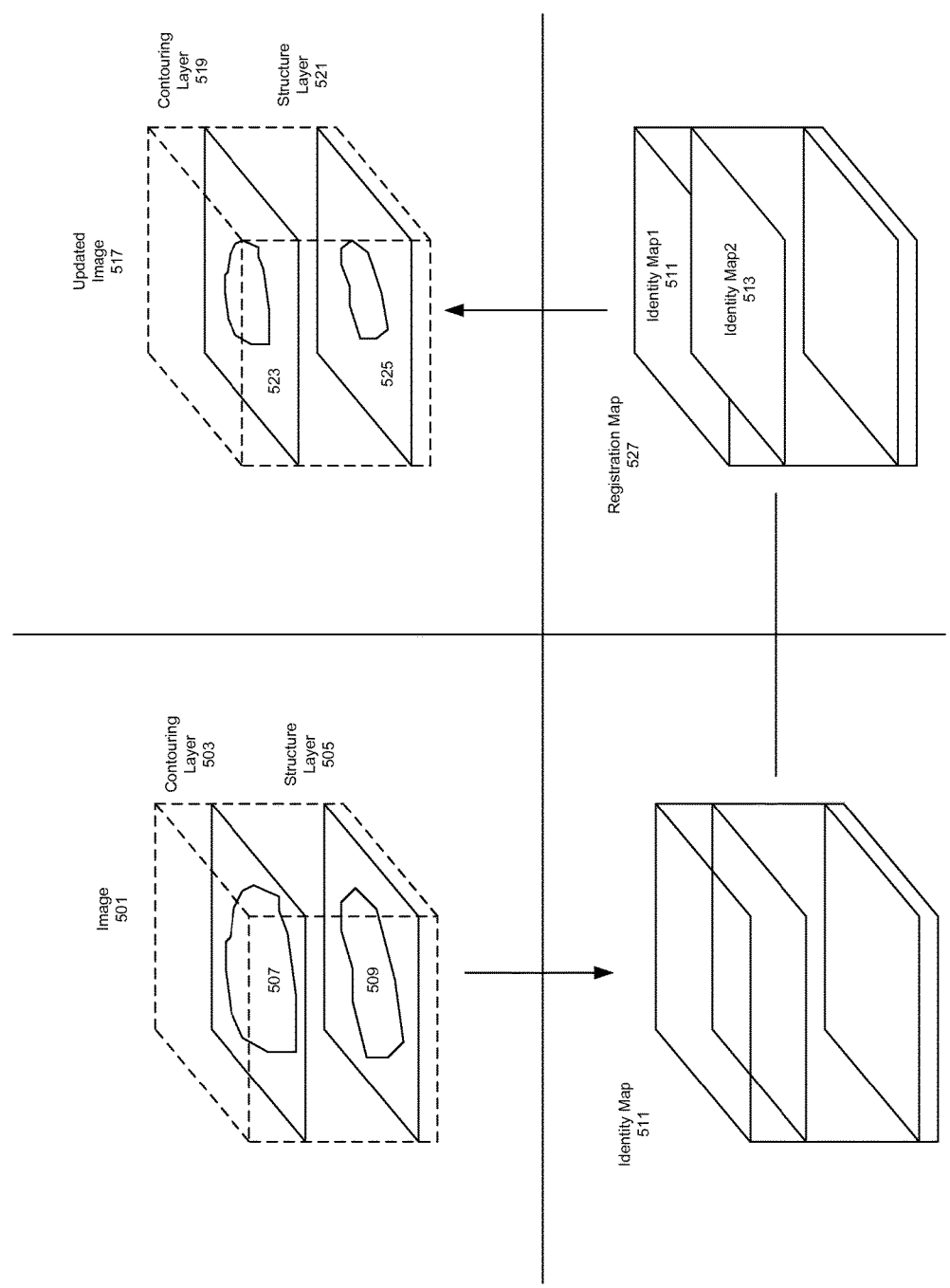
FIG. 5 is an illustration of an exemplary structural editing in a single image, in accordance with embodiments of the present invention.

FIG. 5 is an illustration of simultaneous editing of a plurality of structures in an image 501. According to some embodiments, an image 501 comprising a plurality of layers (e.g., contour layer 503 and structure layer 505), each with one or more effects (e.g., contour effect 507 and structure 509, respectively). According to one embodiment, the image 501 may be the image 301 described above with respect to FIG. 3. In a typical embodiment, data for the image 501 may be a pre-generated image acquired at an earlier point in time and stored as a computer readable medium, for example. As shown in FIG. 5, when one or more of the locally disposed structures comprising the image 501 are edited, the other remaining structures comprising the image 501 may be likewise modified to account for the edited structures, such that a specific, simultaneous editing may be automatically achieved.

In one embodiment, the image 501 may be accessed (e.g., via an image manipulation or image viewing application) and displayed (e.g., through a graphical user interface) to a user. The one or more structures of the image 501 (including contoured effects) may be edited after the image has been referenced. The structures may be edited to add, modify, refine or remove contouring or other structures for example. The editing may be performed through the user interface of the same image manipulation or image viewing application used to view the application. According to one embodiment, when modifications to the structures in image 501 during editing are made, a new identity map 513 is created and a registration map 527 maps the identity map 513 of the updated image to the identity map 511 of the original image.

Once the registration map 527 has mapped the identity maps of the respective original and updated images, the unedited structures in the original image (e.g., image 501) may be modified to reflect and/or account for the edited structures. The modification may be achieved by, for example, applying to each unedited structure the adjustment made to the edited structures modified according to the mapped relationship between the identity maps (e.g., identity map1 511 and identity map2 513) in the registration map 527 to consider the relativity of the structures, thus enabling an automatic and simultaneous editing of each of the structures comprising an image that generates a specific and adaptive output for each structure. The resulting image (e.g., image 517) with modified structures (e.g., 523, 525) may include a corresponding number of layers (e.g., contouring layer 519, structure layer 521) as the first image (e.g., image 501). In addition, the resulting image 517 may be stored with or, alternatively, may replace the original image (e.g., image 501) when referenced at a subsequent time. According to certain embodiments, the deformation mechanism may be implemented as a vector field.

Exemplary Automatic Propagation of Edited Structures

Figure 6:
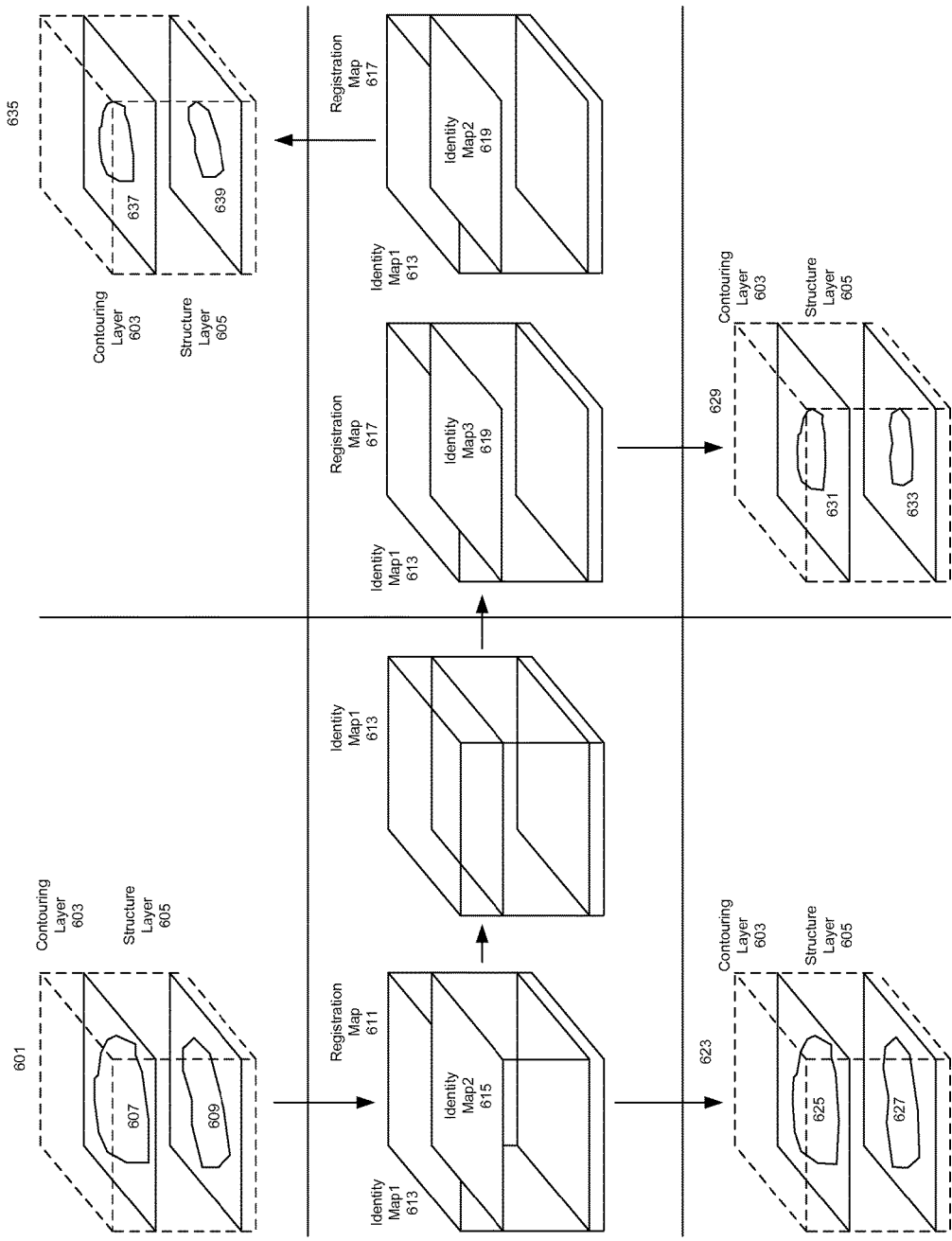
FIG. 6 is an illustration of an exemplary structural editing and propagation in multiple, related images, in accordance with embodiments of the present invention.

According to further embodiments of the claimed subject matter, the automatic propagation properties described above with reference to FIG. 3 can be extended to include manually edited structures, such as the manually edited structures described above with respect to FIG. 4. FIG. 6 is an illustration of automatic propagation of an edited plurality of structures in an image 601. Accordingly, FIG. 6 is depicted as combining features from a process of editing local structures (e.g., the process described above with respect to FIGS. 4 and 5) with a process for automatically propagating modifications to associated images (e.g., the process described above with respect to FIGS. 1-3).

As presented in FIG. 6, an image 601 is provided comprising a plurality of layers (e.g., contour layer 603 and structure layer 605), each with one or more structures (e.g., contour effect 607 and structure 609, respectively). According to one embodiment, the image 601 may be the image 301 described above with respect to FIGS. 3 and/or 5. In a typical embodiment, data for the image 601 may be a pre-generated image acquired at an earlier point in time and stored as a computer readable medium, for example. As shown in FIG. 6, when one or more of the structures comprising the image 601 are edited, the other remaining local structures comprising the image 601 may be likewise modified to account for the edited structures, such that a specific, simultaneous editing may be automatically achieved. In addition, the structures of associated images (e.g., image 635) may also be edited to conform to the edited structure, while accounting for pre-existing dissimilarities. For example, images of the same structures (e.g., anatomy) taken over a period of time that exhibit progress (or regress) may depict those structures in drastically different sizes, shapes, and orientations. This may be particularly true of areas targeted for radiation treatment. Accordingly, editing a structure in one image (e.g., an image obtained during the treatment planning or diagnostic stage) may not produce completely appropriate and/or accurate results to apply a direct equivalent editing in a later image.

As depicted in FIG. 6, editing local structures of a first image (e.g., image 601) may be performed as described above in FIG. 5. According to certain embodiments, images of different data sets or even corresponding to different image standards may be likewise affected. For example, the image 601 may be generated from a computer tomography (CT) image device. Likewise, an image of the same or substantially similar portion of a target anatomy displayed in image 601 may be likewise generated by an image device of a separate standard or method. For example, a cone-beam computer tomography (CBCT) image device may be used to generate CBCT images of the same or substantially similar portion of the target anatomy.

According to certain embodiments, manual structural editing may be propagated to images between the disparate standards. Thus, a CBCT image (e.g., image 623) associated with a CT image (e.g., image 601) and displaying common structures (e.g., structure 625 and 627) may also be automatically modified to according to the same relativity (e.g., captured in a registration map 611) mapped between the structures the identity map1 613 of the first image 601 and the identity map2 615 of the image 623, resulting in a modified CBCT image (e.g., image 629) with edited structures (e.g., structure 631 and 633).

Thus, when the identity map 613 mapping the structures of the first image 601 is modified (e.g., by editing one or more structures of the first image 601), the identity map 613 may be compared to an identity map 619 generated from the modification to one or more structures of the first image 601. The edited structures may be subsequently mapped to corresponding structures of the first identity map 613 (e.g., in a registration map 617). Unedited structures from the first identity map 613 may be duplicated in the generated identity map 619 while being adjusted according to the same relativity mapped between the structures of the first identity map 613 and the manually edited counterparts in the new identity map 619.

Thus, for example, a structure such as a tumor or mass that has been edited to be of a reduced size may cause an associated structure, such as a manually contoured target volume, to be of proportionally reduced size. These modifications to the identity map 613 may alter the image displayed (e.g., in a display device to the editing user). As presented, the modifications to the identity map 613 may be displayed as a resulting image 635, with corresponding edited structures (e.g., structure 637 corresponds to structure 607, and structure 639 corresponds to structure 609). Accordingly, the specific propagation of contoured effects and manually edited structures may be automatically propagated to other local structures as well as affiliated images.

Exemplary Computing Device

Figure 7:
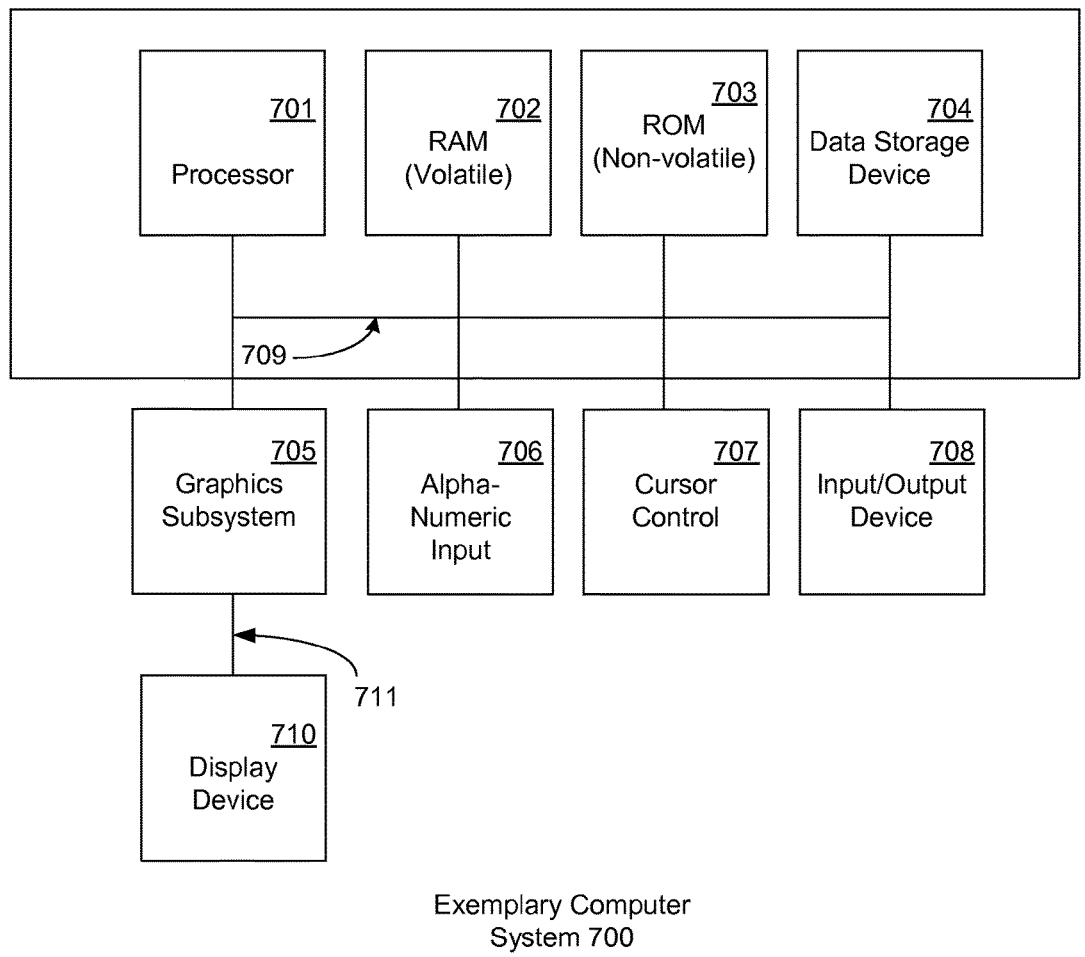
FIG. 7 depicts an exemplary computing environment, in accordance with embodiments of the present invention.

As presented in FIG. 7, an exemplary system upon which embodiments of the present invention may be implemented includes a general purpose computing system environment, such as computing system 700. In its most basic configuration, computing system 700 typically includes at least one processing unit 701 and memory, and an address/data bus 709 (or other interface) for communicating information. Depending on the exact configuration and type of computing system environment, memory may be volatile (such as RAM 702), non-volatile (such as ROM 703, flash memory, etc.) or some combination of the two.

Computer system 700 may also comprise an optional graphics subsystem 705 for presenting information to the computer user, e.g., by displaying information on an attached display device 710, connected by a video cable 711. According to embodiments of the present claimed invention, the graphics subsystem 705 may be coupled directly to the display device 710 through the video cable 711. A graphical user interface of an image viewing software application executing in the computer system 700 may be generated in the graphics subsystem 705, for example, and displayed to the user in the display device 710. In alternate embodiments, display device 710 may be integrated into the computing system (e.g., a laptop or netbook display panel) and will not require a video cable 711. In one embodiment, the processes 100, 200, and 300 may be performed, in whole or in part, by graphics subsystem 705 in conjunction with the processor 701 and memory 702, with any resulting output displayed in attached display device 710.

Additionally, computing system 700 may also have additional features/functionality. For example, computing system 700 may also include additional storage (removable and/or non-removable) including, but not limited to, magnetic or optical disks or tape. Such additional storage is illustrated in FIG. 7 by data storage device 707. Computer storage media includes volatile and nonvolatile, removable and non-removable media implemented in any method or technology for storage of information such as computer readable instructions, data structures, program modules or other data. RAM 702, ROM 703, and data storage device 707 are all examples of computer storage media.

Computer system 700 also comprises an optional alphanumeric input device 706, an optional cursor control or directing device 707, and one or more signal communication interfaces (input/output devices, e.g., a network interface card) 708. Optional alphanumeric input device 706 can communicate information and command selections to central processor 701. Optional cursor control or directing device 707 is coupled to bus 709 for communicating user input information and command selections to central processor 701. Signal communication interface (input/output device) 708, also coupled to bus 709, can be a serial port. Communication interface 709 may also include wireless communication mechanisms. Using communication interface 709, computer system 700 can be communicatively coupled to other computer systems over a communication network such as the Internet or an intranet (e.g., a local area network), or can receive data (e.g., a digital television signal).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A radiation therapy device comprising:
   one or more radiation sources;
   one or more imagers configured to receive radiation from the one or more radiation sources, and to generate initial image data comprising one or more anatomical structures and an updated image data comprising the one or more anatomical structures at a subsequent time; and
   a computing device comprising a processor configured to instantiate a user interface, the user interface being configured to receive user input corresponding to a manual contouring data of the one or more anatomical structures in the initial image data, the processor being further configured to edit the one or more anatomical structures based on the manual contouring data, to generate a distinct deformation map for each common image feature deviation within the initial image data and the updated image data, and to propagate the contour data from the initial image data to the updated image data based on the deformation map, the processor being further configured to propagate manual contouring data received for the updated image data to the initial image data based on each deformation map since each deformation map is invertible,
   wherein each common image feature deviation is based on a relativity between an intensity of a first plurality of pixels comprising a common feature of the initial image data and an intensity of a second plurality of pixels comprising the common feature of the updated image data.

2. The device according to claim 1, wherein the processor is configured to automatically propagate the manual contouring data to the updated image data by applying each deformation map to the initial image data and replicating the manual contouring data on to the updated image data while adjusting for each deformation map.

3. The device according to claim 1, wherein the processor is configured to edit the plurality of anatomical structures by creating a radiation application plan for at least a portion of an anatomical structure of the plurality of anatomical structures in the initial image data.

4. The device according to claim 3, wherein the processor is further configured to adapt the radiation application plan to comprise an updated treatment plan based on the updated image data.

5. The device according to claim 4, wherein the processor is configured to adapt the radiation application plan subsequent to propagating the manual contouring data comprised in the initial image data to the updated image data.

6. The device according to claim 3, wherein the one or more radiation sources are configured to apply radiation to a target volume comprised in the one or more anatomical structures according to the updated treatment plan.

7. The device according to claim 1, wherein at least one of the initial image data and the updated image data comprises a computer tomography (CT) scan image.

8. The device according to claim 1, wherein at least one of the initial image data and the updated image data comprises a cone-beam computer tomography (CBCT) scan image.

9. The device according to claim 1, wherein each deformation map is represented as a vector field.

10. The device according to claim 1, wherein the processor is further configured to detect content deviation by comparing pixel data of pixels comprising a common feature in the initial image data to pixel data of the common feature in the updated image data.

11. The device according to claim 1, wherein each deformation map is represented as a three dimensional vector field.

12. A non-transitory computer readable medium comprising a plurality of programmed instructions for implementing, via a processor, the propagation of updated structural contouring data among a plurality of data sets, the programmed instructions comprising:

instructions to acquire initial image data comprising a plurality of anatomical structures;

instructions to receive user input corresponding to a manual contouring data of the plurality of anatomical structures in the initial image data;

instructions to acquire updated image data comprising the plurality of anatomical structures at a subsequent time;

instructions to establish a relationship between the updated image data and the initial image data;

instructions to edit the plurality of anatomical structures in the initial image data according to the manual contouring data;

instructions to generate a distinct deformation map for each common image feature deviation within the initial image data and the updated image data by comparing the initial image data to the updated image data to determine a presence of deviation between the initial image data and the updated image data;

instructions to automatically propagate the manual contouring data comprised in the initial image data to the plurality of anatomical structures in the updated image data based on each deformation map;

instructions to propagate manual contouring data received for the updated image data to the initial image data based on each deformation map since each deformation map is invertible; and wherein each common image feature deviation is based on a relativity between an intensity of a first plurality of pixels comprising a common feature of the initial image data and an intensity of a second plurality of pixels comprising the common feature of the updated image data.

13. The non-transitory computer readable medium according to claim 12, wherein the instructions to edit the plurality of anatomical structures comprises:

instructions to create a treatment plan for at least a portion of an anatomical structure of the plurality of anatomical structures in the initial image data.

14. The non-transitory computer readable medium according to claim 12, wherein the instructions to automatically propagate the manual contouring data to the updated image data by applying each deformation map to the initial image data and replicating the manual contouring data on to the updated image data while adjusting for each deformation map.

15. The non-transitory computer readable medium according to claim 12, wherein the instructions to edit the plurality of anatomical structures comprise instructions to create a radiation application plan for at least a portion of an anatomical structure of the plurality of anatomical structures in the initial image data.

16. The non-transitory computer readable medium according to claim 15, wherein the programmed instructions further comprise instructions to adapt the radiation application plan to comprise an updated treatment plan based on the updated image data.

17. The non-transitory computer readable medium according to claim 16, wherein the instructions to adapt the radiation application plan comprise instructions to adapt the radiation application plan responsive to the manual contouring data comprised in the initial image data being propagated to the updated image data.

18. The non-transitory computer readable medium according to claim 15, wherein the programmed instructions further comprise instructions to apply radiation to a target volume comprised in at least one of the initial image data and the updated image data according to the updated treatment plan.

19. The non-transitory computer readable medium according to claim 12, wherein at least one of the initial image data and the updated image data comprises a computer tomography (CT) scan image.

20. The non-transitory computer readable medium according to claim 12, wherein at least one of the initial image data and the updated image data comprises a cone-beam computer tomography (CBCT) scan image.

21. The non-transitory computer readable medium according to claim 12, wherein each deformation map is represented as a vector field.

22. The non-transitory computer readable according to claim 12, wherein each deformation map is represented as a three dimensional vector field.

* * * * *